United States Patent

Suh et al.

(10) Patent No.: US 7,817,845 B2
(45) Date of Patent: Oct. 19, 2010

(54) MULTI-FREQUENCY IMAGE PROCESSING FOR INSPECTING PARTS HAVING COMPLEX GEOMETRIC SHAPES

(75) Inventors: Ui Won Suh, Cincinnati, OH (US); Gigi Olive Gambrell, West Chester, OH (US); William Stewart McKnight, Hamilton, OH (US); Preeti Pisupati, Bangalore (IN); Peyush Kumar Mishra, Bangalore (IN); Sandeep Kumar Dewangan, Bangalore (IN); Changting Wang, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 922 days.

(21) Appl. No.: 11/617,859

(22) Filed: Dec. 29, 2006

(65) Prior Publication Data

US 2008/0159619 A1    Jul. 3, 2008

(51) Int. Cl.
*G06K 9/00* (2006.01)
*G01R 11/02* (2006.01)

(52) U.S. Cl. ........................ 382/141; 324/137

(58) Field of Classification Search ......... 382/141–152, 382/270; 324/137, 164, 500–537
See application file for complete search history.

(56) References Cited

U.S. PATENT DOCUMENTS

| 3,337,796 | A |   | 8/1967 | Hentschel et al. |
|---|---|---|---|---|
| 3,576,489 | A |   | 4/1971 | Law et al. |
| 4,476,434 | A | * | 10/1984 | Collins et al. ............... 324/233 |
| 5,323,241 | A | * | 6/1994 | Yonezawa .................... 382/167 |
| 5,345,514 | A | * | 9/1994 | Mahdavieh et al. ......... 382/152 |
| 5,770,943 | A | * | 6/1998 | Zhou .......................... 324/307 |
| 6,220,099 | B1 |   | 4/2001 | Marti et al. |
| 6,907,358 | B2 |   | 6/2005 | Suh et al. |
| 6,914,215 | B2 |   | 7/2005 | Davis et al. |
| 7,154,265 | B2 |   | 12/2006 | Togo et al. |
| 7,206,706 | B2 |   | 4/2007 | Wang et al. |
| 7,337,651 | B2 |   | 3/2008 | Shankarappa et al. |
| 7,436,992 | B2 |   | 10/2008 | Suh et al. |
| 7,518,359 | B2 |   | 4/2009 | Wang et al. |
| 7,657,389 | B2 |   | 2/2010 | Suh et al. |
| 7,689,030 | B2 |   | 3/2010 | Suh et al. |
| 2002/0028025 | A1 | * | 3/2002 | Hong .......................... 382/260 |
| 2006/0229833 | A1 |   | 10/2006 | Pisupati et al. |

FOREIGN PATENT DOCUMENTS

| EP | 0445983 | A2 | 9/1991 |
|---|---|---|---|
| EP | 0533440 | A1 | 3/1993 |
| EP | 0577244 | A2 | 1/1994 |
| EP | 1701157 | A  | 9/2006 |

\* cited by examiner

*Primary Examiner*—Anand Bhatnagar
*Assistant Examiner*—Alex Liew
(74) *Attorney, Agent, or Firm*—McNees Wallace & Nurick LLC

(57) ABSTRACT

A method for detecting small cracks and other anomalies on parts having complex geometries is disclosed. The method includes eddy current inspection incorporating collection of data from multi-frequency eddy current signals. Phase analysis is used to combine the multi-frequency data to enhance the signal to noise ratio of the raw inspection image. The image is then reprocessed using a spatiotemporal filter to correlate with the frequency components of the eddy current flaw signal to separate signals associated with cracks and other flaws at edges that would ordinarily be hidden by edge effect signals.

17 Claims, 6 Drawing Sheets

H1

V1

H2

V2

H_MF

V_MF

FIG. 7

MULTI-FREQUENCY IMAGE PROCESSING FOR INSPECTING PARTS HAVING COMPLEX GEOMETRIC SHAPES

FIELD OF THE INVENTION

The present invention is generally directed to methods of inspecting components using eddy currents and more particularly to methods of inspecting components using eddy currents through the use of image processing.

BACKGROUND OF THE INVENTION

Eddy current inspection is a commonly used technique for detecting discontinuities or flaws in the surface of a gas turbine engine component. Eddy current techniques are based on the principle of electromagnetic induction in which eddy currents are induced within the material under inspection. Eddy currents are induced in a test specimen by alternating magnetic fields created in the coil of an eddy current probe when the probe is moved into proximity with the component under test. Changes in the flow of eddy currents are caused by the presence of a discontinuity or a crack at or near the surface of the specimen under test. The altered eddy currents produce a secondary field which is received by the eddy current probe coil or by a sensor coil in the eddy current probe which converts the altered secondary magnetic field to an electrical signal which may be recorded on a strip chart. An eddy current machine operator may then detect and size flaws by monitoring and reading the signals recorded on the strip chart. Flaws or defects are detected if the electrical signal exceeds a predetermined voltage threshold.

Present eddy current inspection methods work satisfactorily when the components under inspection have simple geometrical shapes, such as holes, flat plates or the like. However, when the component under test has a complex geometrical shape, such as the dovetail slots of a high pressure or low pressure turbine disk, fan disk, high pressure compressor disk, teeth of a gear or the like, the complex geometry of these components such as edges and transitions between convex, concave and flat regions, produces contributions to the eddy current signals which make it difficult to distinguish between defects and geometric effects.

Such complex geometric features can produce larger eddy current signals than the signals from a specific crack or flaw of interest. This makes it difficult to distinguish geometric edge signals, for example, from a crack or seam, especially when using a signal amplitude basis for accepting or rejecting parts.

One attempt at solving this problem is described in U.S. Pat. No. 5,345,514, which builds real time images from identical, repeated geometries in a part. After the collection of several of these images, a subtraction process is initiated that subtracts the images from adjacent features. While this reduces the dominant edge signals that are common to adjacent features, it does not eliminate them due to geometric variation from feature to feature within a single part. If only one feature is to be inspected, the method does not work because there are no repeated images to subtract.

Conventional, single probe eddy current inspections have utilized numerous filtering techniques that distinguish between relevant and non-relevant signals, or filter out signals from different portions of the frequency spectrum. Yet none of these techniques have been satisfactory in reducing or eliminating edge and other geometry signals.

What is needed is a method of eddy current inspection that can recognize meaningful signals related to geometry and delete or distinguish them from spurious signals that represent cracks and other important information about the integrity of the part under test.

SUMMARY OF THE INVENTION

According to an exemplary embodiment of the invention, a method for inspecting a part is disclosed. The method comprises providing a part having a non-planar surface, providing an eddy current apparatus, acquiring multi-frequency data for the surface of the part at two different phases, forming a raw inspection image of the surface using the multi-frequency data, enhancing the raw inspection image by phase analysis, and reprocessing the enhanced image using a spatio-temporal filter.

According to another exemplary embodiment of the invention, a method for inspecting a part comprises providing a part having an edge, providing an eddy current apparatus, acquiring phase data for at least two phases in at least two different frequencies for the part under inspection using an eddy current probe, combining the first phase data into a first single multi-frequency phase image having a plurality of pixels, combining the second phase data into a second single multi-frequency phase image having a plurality of pixels, preprocessing each of the first and second multi-frequency phase images, performing a spatio-temporal correlation on each preprocessed phase image to produce a correlation feature, performing a thresholding operation on the correlation feature of each preprocessed phase image to produce a binary first phase image and a binary second phase image, and combining the produced binary images to generate a single image.

One exemplary embodiment of the invention permits inspection of parts having a complex geometry, including edges, without compromising eddy current signals from relevant indications. It may also minimize the amount of time needed to acquire, process the data, and properly evaluate indications resulting in significant improvement in the sensitivity of the inspection compared to other inspection methods.

Another exemplary embodiment of the invention provides improved inspection sensitivities by reducing or eliminating undesirable aspects of the eddy current signal that can mask or conceal defect detection. Of particular benefit is the improved capability to inspect critical component features up to and including its edges, which are notorious as stress concentration locations where cracks are likely to occur, but which also represent the most likely regions for signal aspects that mask defects.

Methods according to exemplary embodiments of the invention method eliminate the need for any reference images to suppress the undesired signals arising due to geometric features of the part, edge signals and any other inspection related noise. This improves the speed and reliability of the inspection and makes the inspection process also applicable for cases where a reference sample for the inspection is unavailable. It further eliminates the error associated with the inherent variation between the inspected feature and the nearby reference feature.

Exemplary embodiments of the invention can be implemented on a PC-based workstation or similar micro-processor based platform, and the associated eddy current inspection can be run and processed on a real-time basis.

Enhanced defect characterization enables the 90/50 probability of detection to extend to smaller indication size ranges than other methods.

Other features and advantages of the present invention will be apparent from the following more detailed description of exemplary embodiments, taken in conjunction with the accompanying drawings which illustrate, by way of example, the principles of the invention.

BRIEF DESCRIPTION OF THE DRAWINGS

FIG. 7 illustrates a portion of a two-dimensional digital image showing individual pixels.

Where like parts appear in more than one drawing, it has been attempted to use like reference numerals for clarity.

DETAILED DESCRIPTION OF EXEMPLARY EMBODIMENTS

Exemplary embodiments of the invention relate to eddy current imaging-based inspection for use in a variety of different applications, including medical systems, the automotive industry, the aviation industry, or any other application in which non-destructive evaluations are conducted.

Exemplary embodiments of the invention identify characteristics in the eddy current signal that are associated with edges or other undesired geometric or contamination effects. A mathematically modeled signature characterizes eddy current signals arising from flaws on parts. The model simulates the eddy current signal by inputting parameters such as probe geometry, inspection speed, and flaw configuration. By knowing the shape and frequency component of the eddy current flaw signal, non-relevant eddy current signals can be identified and discriminated.

A spatio-temporal filter is applied to correlate with the frequency components that are closer to the eddy current flaw signal frequency than any other non-relevant signal frequencies arising from geometry, contamination, material or surface-related noise. An automated thresholding algorithm is used to suppress most of the non-relevant signal frequencies, while the remaining signal frequencies that correlate well with filter parameters mimic the eddy current flaw signal. However, a relevant flaw signal may still be missed, i.e. a "True Negative," or a non-relevant indication may be identified as a true indication, a "False Positive."

"True Negatives" usually occur when the signal strength relative to the other background information is not enough to correlate with the filter parameters, that is, there is a low signal to noise ratio (SNR). To minimize the "True Negatives," exemplary embodiments of the invention introduce a multi-frequency and phase analysis approach to combine data acquired from multiple frequencies for enhancing the SNR of the raw inspection image data, which is later processed using a spatio-temporal filter for indication identification.

"False Positives" usually occur either when there are strong indications arising due to inspection noise or when the noise patterns randomly match with the filter parameters that are used to characterize flaw patterns. A false call reduction algorithm eliminates such left over signals based on the signature pattern analysis of the identified region. The signal processing techniques eliminate these signals associated with unwanted features, leaving only the indications that are relevant.

A transfer function may be used to characterize and/or size the relevant indications identified. The transfer function takes different features derived from the identified indication as its input and returns an equivalent flaw size measure as output.

Figure 1:
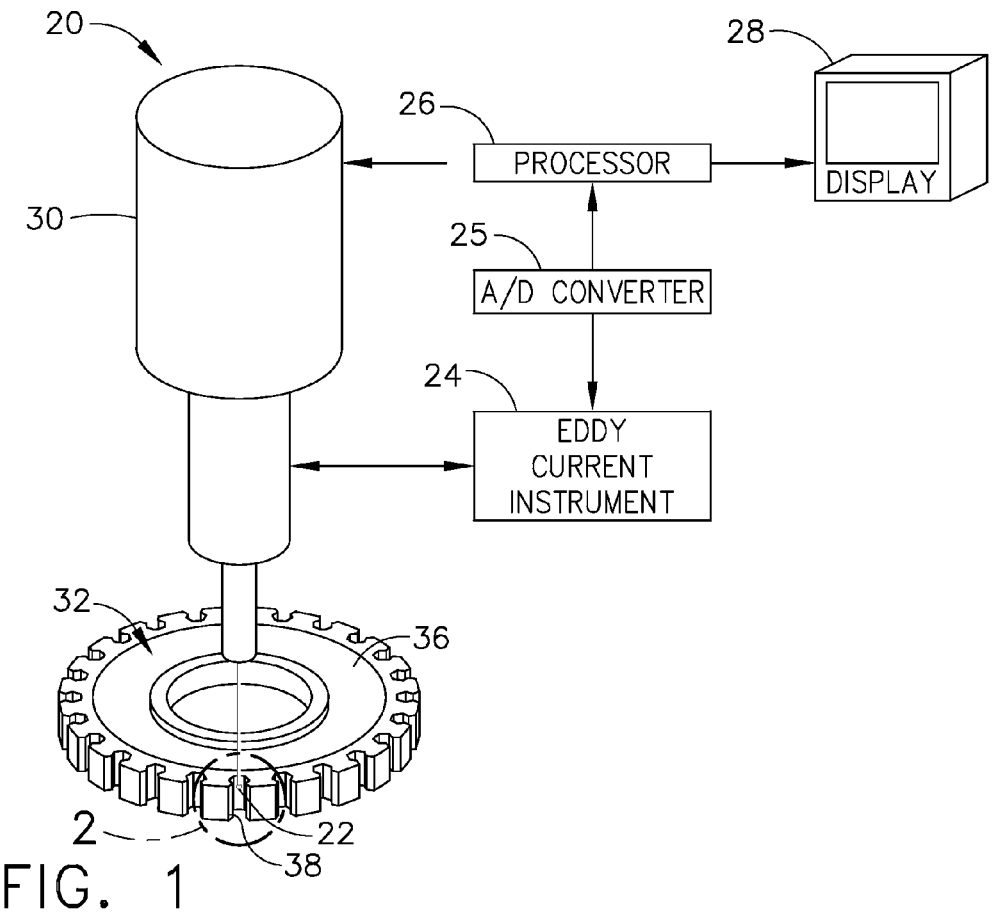
FIG. 1 schematically depicts an eddy current inspection system for a non-planar part with an edge.

FIG. 1 depicts an exemplary inspection system 20 for performing the inspection of non-planar parts. As used herein, a "part" includes any object being inspected by the present approach, including but not limited to articles, components, structures, test specimens, and the like. A "non-planar part" is such an object wherein the surface of the region of the part being inspected is not planar. That is, it has an edge, a contour, or other non-planar surface feature. The non-planar "part" of FIG. 1 depicts a dovetail arrangement in a disk.

The inspection system 20 includes an eddy current probe 22, an eddy current instrument 24, an analog to digital (A/D) converter 25, a processor 26, and a display 28, all in communication with one another, such as by cabling. The physical configuration of such inspection systems 20 is known in the art, except for the improvements discussed herein. The eddy current probe 22 is configured to induce eddy currents in a non-planar part 32, here a disk, and to measure the resulting eddy current response signals, in order to inspect the non-planar part 32. Such eddy current probes are known in the art.

The eddy current probe 22 may be stationary or, preferably, may be moved relative to the non-planar part 32. The movement of the eddy current probe 22 relative to the non-planar part 32 may be accomplished manually or in an automated fashion. The eddy current probe 22 is optionally but preferably mounted on a scanner 30 that positions and moves the eddy current probe relative to a stationary non-planar part 32. (Alternatively, the non-planar part 32 may be moved and the eddy current probe 22 held stationary.) The optional scanner 30 may be of any type, but is typically a multi-axis numerically controlled device controlled by the processor 26. In the embodiment shown in FIG. 1, the scanner 30 provides translation and rotation of the eddy current probe 22 as may be required for the specific type of non-planar part 32. The scanner 30 precisely positions the eddy current probe 22 relative to the non-planar part 32 and moves the eddy current probe 22 in a stepped, rastered fashion.

Figure 2:
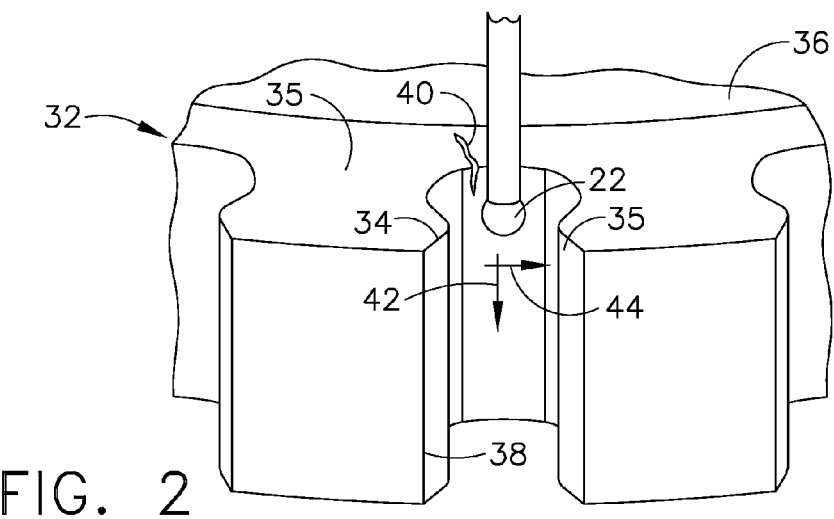
FIG. 2 is a schematic detail, taken in region 2 of FIG. 1, showing the dovetail feature being inspected.

As shown in FIG. 2, the non-planar part 32 has a non-planar edge 34 thereon as an example of a non-planar surface 35, and the inspection is conducted at or near the edge 34. As used herein, "at or near" means that an eddy current response signal (i.e., the signal of interest) of any anomaly in the non-planar part 32 has its signal-to-noise ratio reduced by an eddy current response signal (i.e., noise) of the non-planar surface 35 of the non-planar part 32, in this case the non-planar edge 34. An "anomaly" is a feature of interest that is detectable above the background noise by the eddy current technique and whose signal-to-noise ratio may be improved by the present approach. Examples of anomalies include cracks, incipient cracks, inclusions at or near the surface, particles at or near the surface, porosity, voids and the like. The presence of the non-planar edge 34 produces noise in the eddy current response signals, and the present approach improves the signal-to-noise ratio of the eddy current response signals.

There are a large number of types of non-planar parts 32 that may have contours or edges 34 thereon. In the illustrations of FIGS. 1 and 2, the non-planar part 32 is a turbine disk 36, and the inspected non-planar surface 35 is a portion of a disk slot 38 formed along the outer periphery of the turbine disk 36, the slot 38 having an edge 34. Other types of non-planar surfaces include, for example, machined or cast edges between a front and a side of the non-planar part, a leading edge of an airfoil (such as a turbine blade or vane), a trailing edge of the airfoil, a blade root of the airfoil, intentionally produced holes such as fastener holes or large bores, and openings such as cooling holes. In the present approach, the eddy current probe 22 may have any configuration operable for the type of non-planar part 32 being inspected. The physical configuration and electrical characteristics of the eddy current probe 22 are typically optimized for each type of non-planar part 32.

The edge 34 has an associated stress concentration when loaded in service. Consequently, anomalies such as a crack 40 illustrated in FIG. 2 may preferentially initiate at or near the edge 34. The crack 40 is illustrated as a surface edge crack, but it may be a surface near-edge crack, or a subsurface edge or near-edge crack as well. The eddy current inspection system 20 is used to detect such a crack 40 at an early stage. Once detected after reaching a resolvable size, the crack 40 may be repaired using known techniques, or, if the crack 40 cannot be repaired, the non-planar part 32 is removed from service. The noise that is otherwise present in the eddy current response signal associated with the edge 34 tends to mask the presence of the crack 40.

Figure 3:
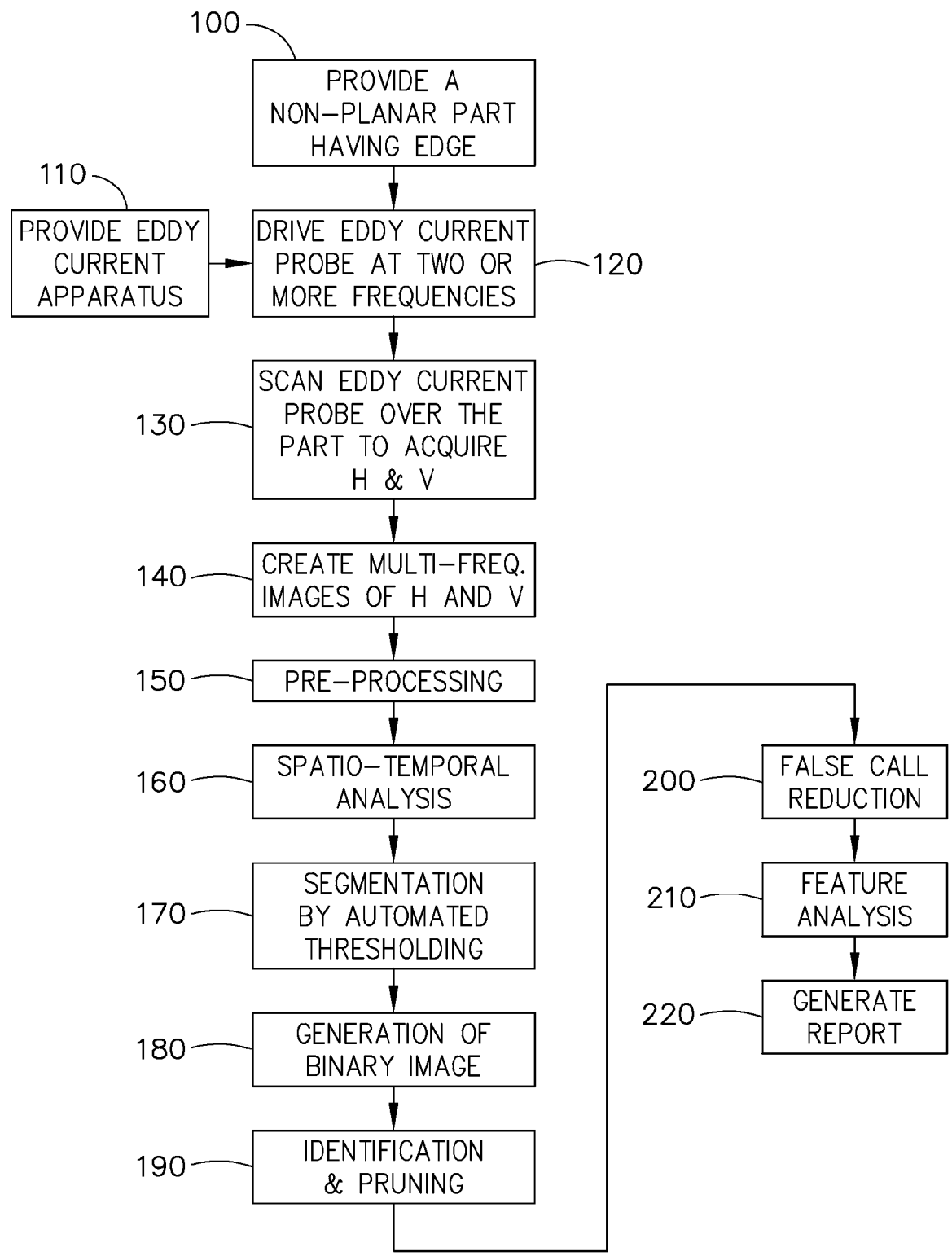
FIG. 3 is a block flow diagram of an embodiment of a method for practicing the present invention.

FIG. 3 depicts the steps in an embodiment of the present approach. The non-planar part 32 having the edge 34 is provided, step 100. The eddy current apparatus, including the eddy current probe 22, the eddy current instrument 24, the processor 26, and preferably the display 28, is provided, step 110. The eddy current probe 22 is positioned adjacent the non-planar part 32, as illustrated in FIGS. 1 and 2. In general, when the eddy current probe 22 is driven with an alternating-frequency current, alternating magnetic fields are produced in the coil(s) of the eddy current probe 22. In one embodiment, the probe 22 has a single coil. In another embodiment the probe 22 has two coils. Eddy currents are responsively produced in the non-planar part 32. These eddy currents are regular in form, except when they are disturbed by the presence of the crack 40 (an example of an anomaly). The eddy current produces a secondary electrical field, which is measured by the eddy current probe coil or by other types of sensors in the eddy current probe as an eddy current response signal. The measured eddy current response signal is converted to an electrical output, which in turn is provided to the eddy current instrument 24 and thence to the processor 26 for analysis.

In the present approach, the eddy current probe 22 is driven at two or more frequencies, step 120. For the illustration, a single pair of two frequencies, $f_1$ and $f_2$, are used, but additional other pairs of frequencies $f_3 \ldots f_n$ may be selected. The eddy current probe 22 is preferably driven simultaneously with all of the frequencies, but it may be driven sequentially with these frequencies. The selected frequencies may be any two or more frequencies that are operable in an eddy current inspection system. It will be appreciated that selection of specific frequencies to be used depends upon considerations such as the size and type of the anomaly being sought, the geometry of the non-planar part, the material from which the non-planar part is made, eddy current signal characteristics, and other considerations.

The processor 26 is configured to analyze the output of the eddy current instrument 24, and thence the eddy current probe 22, as will be described next.

The eddy current probe 22 is scanned in a series of steps over the non-planar surface 35 of the non-planar part 32, step 130, to acquire channel data at two different phases for each of the frequencies driving or exciting the eddy current coil. In one embodiment, the eddy current probe 22 is incrementally scanned in a vertical (or V) direction 42 in a series of discrete steps and thereafter indexed in a horizontal (or H) direction 44 (although it will be appreciated that scanning could be horizontal with vertical indexing as long as substantially complete coverage of the surface is provided in either case) to acquire channel data at two different phases (e.g. H and V) for each of the frequencies driving or exciting the eddy current coil. The discrete steps in the vertical direction 42 are then repeated at the new index location. This process is repeated until desired coverage of the non-planar surface 35 of the non-planar part 32 is achieved. This scanning process is managed by the scanner 30 under programmed control of the processor 26.

Figure 7:
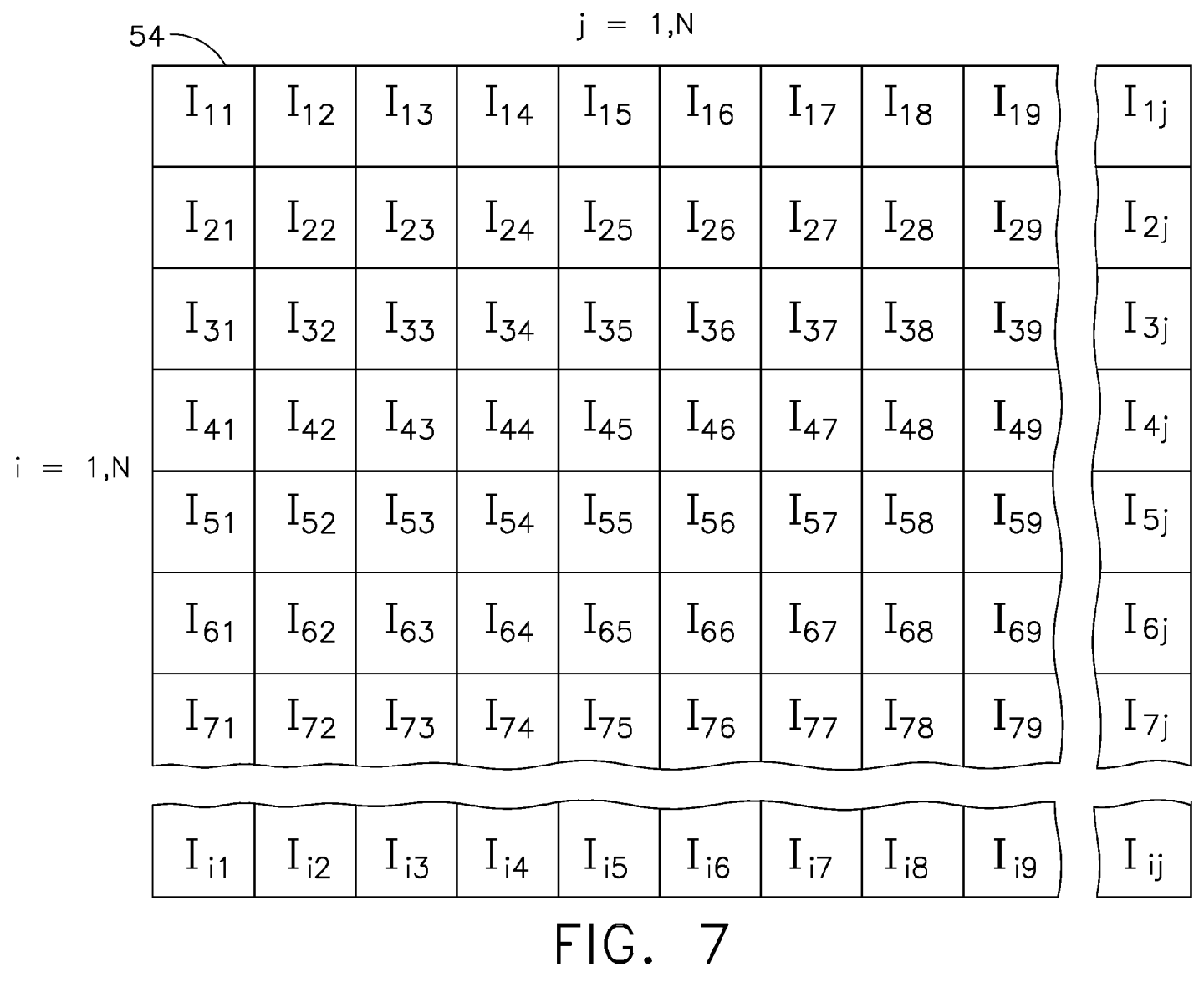

As previously discussed, the analog eddy current signals from the eddy current probe 22 are converted by the A/D converter 25 to digital signals that are stored by the processor 26 and combined after the scanning operation of each non-planar surface 35 to provide a two-dimensional digital image. Each of the two-dimensional images includes a multiplicity of picture elements or pixels 54 as illustrated in FIG. 7. The pixels 54 are usually arranged in uniform columns and rows to form an X-Y matrix type structure. Each of the pixels has a gray scale intensity ($I_{ij}$) which corresponds to the eddy current signal at the location on the surface 35 represented by the particular pixel 54 or group of pixels; thus, changes in the gray scale intensity of the pixels 54 making up the image results from local changes caused by the induced eddy currents. Changes in the component geometry such as edges, transitions between convex, concave and flat surfaces, other surface anomalies and flaws or defects will cause local changes in the eddy current signal which results in differences in the gray scale intensities ($I_{ij}$) of the pixels composing the two-dimensional digital images at those locations in the image corresponding to where the part geometry changes or where a defect or flaw is located.

H channel data from multiple frequencies is combined to one multi-frequency H image, step 140, that may be displayed to the display 28. Likewise, V channel data from multiple frequencies is combined to one multi-frequency V image. The mixing of the multiple frequency data is achieved by the phase rotation and scaling of the H and V components in the impedance plane. The goal of this image mixing step is to improve the signal to noise ratio (SNR) of the smallest detectable feature from the crack 40. Thus, the output of this mixing is two separate images that represent the effective H and V components from different frequencies, respectively, in which the SNR is improved as compared with the individual frequencies. As used herein, "SNR" is defined as follows:

$$SNR = \frac{(\max(\text{abs}(ROI)) - \min(ROI))}{(\max(\text{abs}(BCK)) - \min(BCK))}$$

where ROI is the region of interest

BCK is the region that represents background or noise

Figure 5:
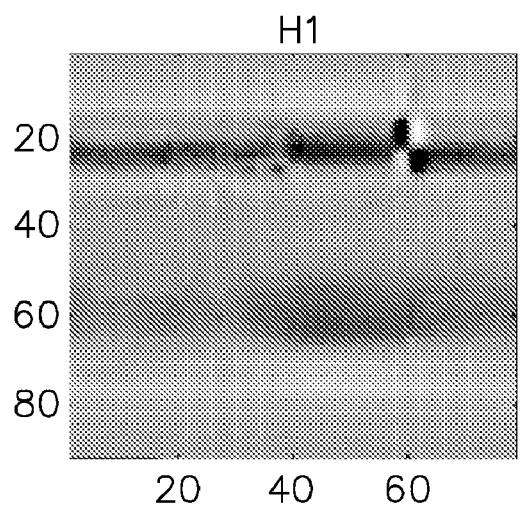
FIG. 5 illustrates single frequency and multi-frequency horizontal and vertical images generated in accordance with a method for practicing the invention.
Figure 5:
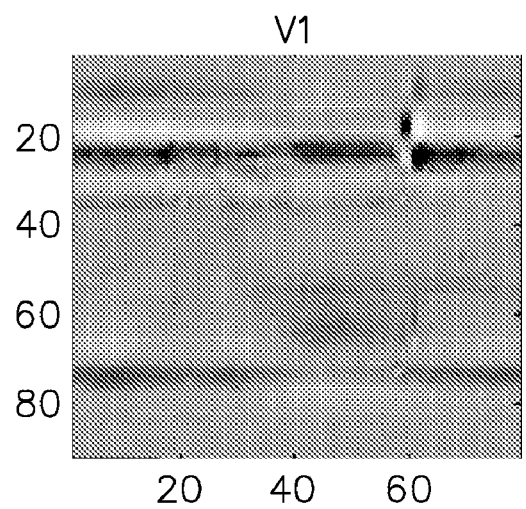
Figure 5:
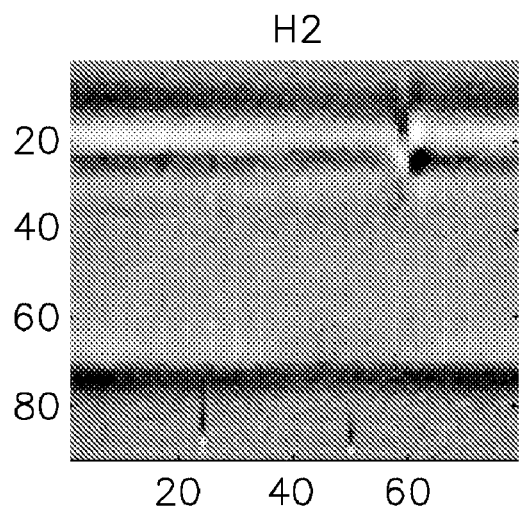
Figure 5:
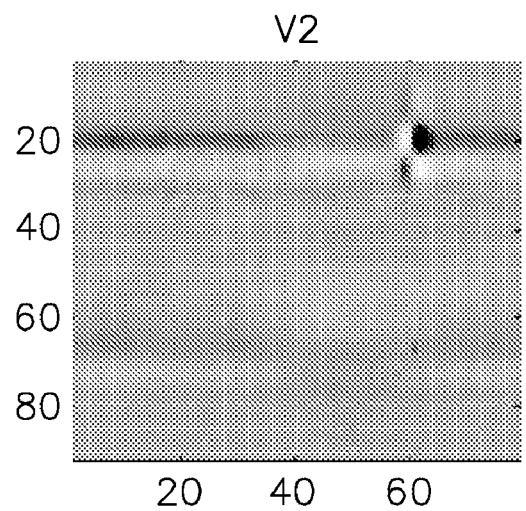
Figure 5:
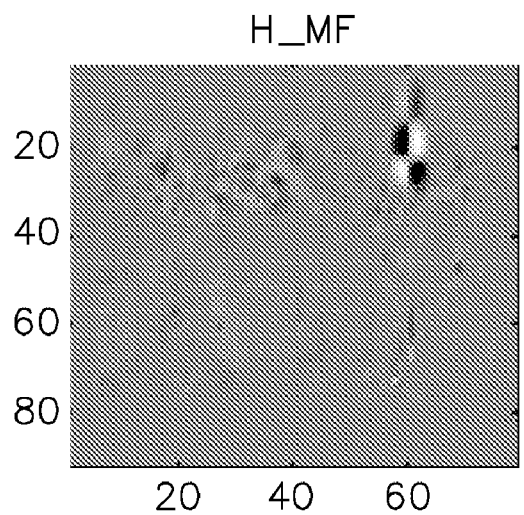
Figure 5:
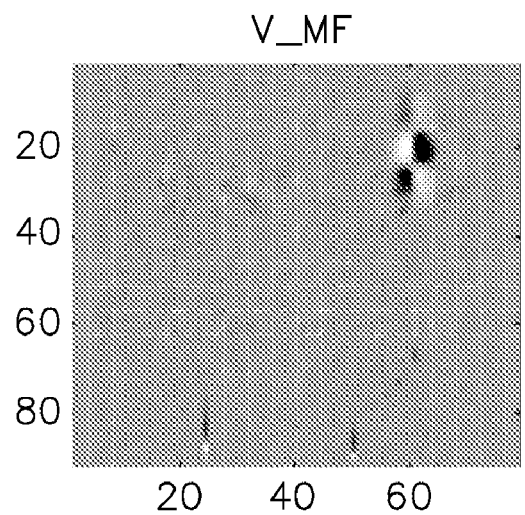

FIG. 5 illustrates images for each of a single pair of frequencies in two phases (H1, H2 and V1 and V2) and the combined multi-frequency images for each phase (H_MF and V_MF). While the characteristic anomaly signature (here the checkerboard pattern from an actual inspection image is shown) appears in each of the single frequency H and V images, the images are accompanied by significant noise (e.g., changes in grayscale that extend horizontally across each image as lines). While the multi-frequency images still have some residual noise (e.g., pixilated regions near the checkerboards) that must be eliminated by further processing for satisfactory identification and characterization of relevant indications, they reduce much of the original noise present in each of the single frequency images.

Typically, but not necessarily, each of the multi-frequency H and V images are preprocessed by applying one or more filters to enhance each image for noise and artifact removal, step 150. This may include engaging a suitable low pass filter to estimate edges that show up as low frequency components and remove them. A de-blurring filter or other noise removal filter may be applied to remove speckle noise. A high pass filter may be used to remove high frequency noise that may arise from the instrumentation. Appropriate smoothing filters may be used to help remove any remaining artifacts after one or more of the above-referenced filter operations are completed and may also restore any significant defect characteristics that are present in the image. The output of the pre-processing results in a multi-frequency H and a multi-frequency V image, each of which have been enhanced to remove noise and artifacts and thereby enhancing relevant, remaining indications better suited for further analysis.

Following any pre-processing steps, each multi-frequency H and V image is subjected to image processing using a spatio-temporal correlation analysis with a designed filter whose parameters are tuned to the frequency characteristics of the anomalous signature that is of interest, step 160. Spatio-temporal filter parameters can be calculated from inspection parameters. From the deconstructed images obtained by the prior steps, this analysis removes non-relevant signals from sources such as material noise, contamination or geometry changes so that only eddy current signals from relevant indications are presented. That is, each preprocessed multi-frequency image is analyzed with respect to space and time in light of specific parameters that relate to the type of inspection being conducted to produce a correlation feature.

The spatio-temporal analysis may be accomplished in two steps. First, the raw image is deconstructed into several images with different frequency components. An original raw image is processed with two-level processing that produces five frequency components. The first component is low pass convolution, the next two are the result of high and medium band pass in a horizontal direction and the remaining two are the result of high and medium band pass in a vertical direction. From the five deconstructed images, frequency components relating to part geometry features are filtered out and only relevant information is left for further processing. Second, the image is reconstructed with the frequency components that are relevant to eddy current flaw signals. Of the five processed components, generally only a few are actually used for reconstructing the image for flaw detection. The reconstructed image has edge signals removed and flaw signals remaining which further improves the SNR.

Figure 4:
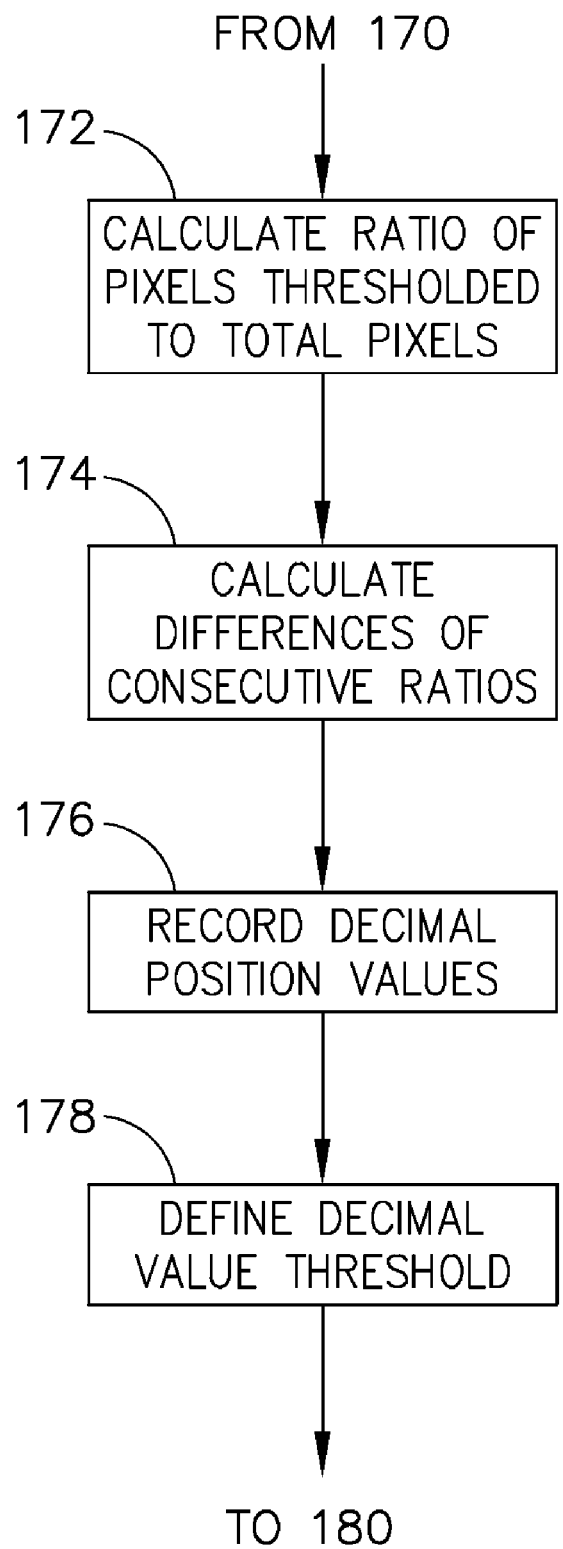
FIG. 4 is a block flow diagram of an embodiment of a sub-routine of a method for practicing the present invention.

An automated thresholding operation, step 170, is performed on the correlation feature that results from the spatio-temporal analysis for each of the H and V multi-frequency images. This operation segments out the potential defect regions. The threshold value selected adapts itself to the kind of signal provided based on statistics of the image under analysis. In one embodiment, the threshold selection process is achieved in the following sub-steps, illustrated in FIG. 4.

The ratio (R) of the number of pixels thresholded of the image under consideration is calculated with respect to the total number of pixels in that image by varying signal threshold by a small incremental amount, step 172. For example, let $R=\{R_1, R_2 \ldots R_n\}$ for a set of ratio values calculated at signal values $\{S_1, S_2 \ldots S_n\}$. Thus, the ratio R for any given signal value can be defined according to the following equation:

$$\text{Ratio} = \frac{\text{No. of pixels thresholded}}{\text{Total no. of pixels}}$$

Next, the difference between two consecutive ratio values is calculated: $R_{i-j}=\{R_1-R_2, R_2-R_3 \ldots R_{n-1}-R_n\}$, step 174. This ratio difference is zero if the signal increment does not add any extra pixels. A high decimal change in ratio indicates that a small difference in signal led to a large number of pixels to be added to the thresholded values.

Decimal position values of the ratio differences are recorded, step 176, for a set of decimal points, $D=\{D_{1-2}, D_{2-3} \ldots D_{(n-1)-n}\}$, in which D is an integer that represents the first significant digit in the difference calculated in step 174. For example, if $R_1-R_2=0.00067$, then $D_{1-2}=4$, the first significant decimal position value; similarly if $R_2-R_3=0.00325$, then $D_{1-2}=3$. The decimal position value is an indication of percentage of pixel variation.

In the event that $D_{i-(i+1)}=0$, it may be replaced with $D_{(i-1)-i}$ which aids in the segmentation process.

From the application domain knowledge, a particular decimal value $d \in \{D\}$ is defined that specifies a significant change in the signal level, step 178. The threshold value that is reported is the signal value $S_i$ that corresponds to the signal level at which the decimal place value 'd' is encountered first. The decision criteria 'd' to select the threshold can be customized based on the application.

The thresholding operation thus includes removal of background regions from identified regions. Identified regions are the regions that were identified in the pre-processing steps. Generally, the background region is represented by a gray scale value of zero and the identified regions are represented by a gray scale value of one. Thus, if a distance between two or more identified regions is less than the selected threshold value determined in steps 172-178, gap filling is performed. Gap filling is a technique by which the gray scale value of a background region in the image between two identified regions of interest is changed. Thus, the output of step 170 is a binary thresholded image for each of H and V.

Returning to FIG. 3, at step 180, the binary images from H and V are combined to a single binary image through a selective region overlapping process by computing the union and intersection of each of the two binary images. At this step, some of the identified regions can be dropped from further processing if they do not meet the necessary criteria to be identified as a potential defect region. The output of this step is a single binary image that consists of various highlighted regions.

Figure 6:
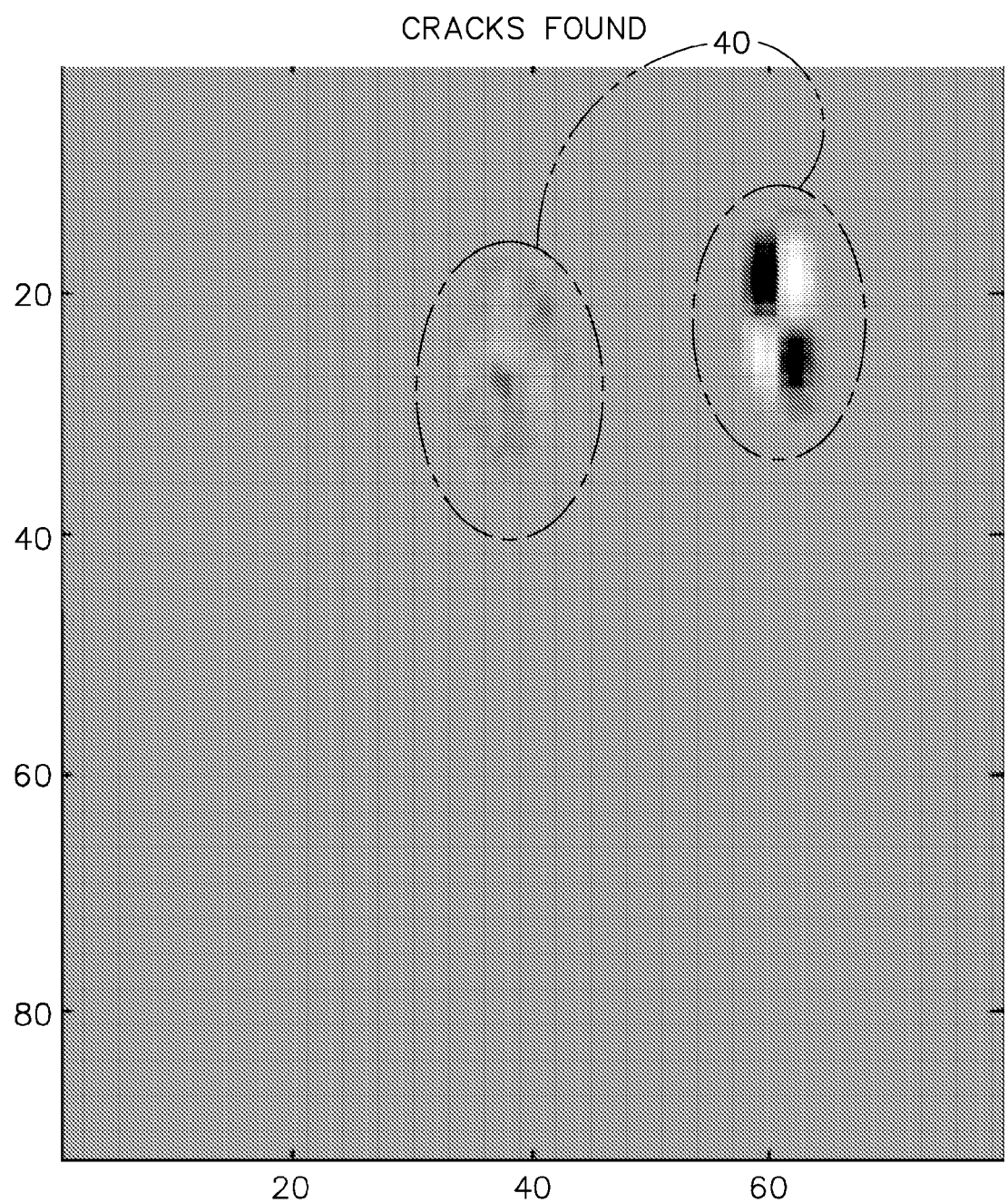
FIG. 6 illustrates a combined image generated in accordance with a method for practicing the invention.

Once the single binary image has been produced, the highlighted regions of interest in the binary image may be trimmed or pruned and approximated to a rectangular shape, step 190. Each of the identified regions is then tested for a checkerboard pattern, which is a characteristic anomaly signature, step 200, to reduce any false calls, i.e. "False Positives." FIG. 6 illustrates a product image of the invention that shows a single binary image that illustrates two anomalies 40, one of which was not apparent from the noise in any of the horizontal or vertical images.

Features such as the maximum signal amplitude, number of pixels, energy contained, entropy and other attributes that represent the signature of the signal may be computed from each of the identified checkerboard regions still under consideration, step 210. In one embodiment, a transfer function (e.g., an A-hat function) that incorporates one or more of these features may be used to provide an estimate of the anomaly size for each of the identified regions. The features can be either one-dimensional or two-dimensional, based on the signal characteristics and the dimensions of the closed shape. In one embodiment, the dimensions of the closed shape are used to suppress false flaw regions. The A-hat value which uses the above features can be used to characterize the flaw. In one embodiment, the defect characterizing parameter is represented by the features like energy and entropy. Thus, the A-hat value may be calculated as a function of the maximum and minimum amplitudes, the energy, entropy, pixels, and phase of the identified region.

The anomalies identified, along with any features and size estimates, may be reported, step 220, although it will be appreciated that the existence of anomalies may be reported at any time. Features and size estimates may be of interest for the part under inspection, which is typically unknown until after the additional processing steps.

Methods in accordance with exemplary embodiments of the invention do not require reference parts or reference images to detect and characterize the flaws. Hence, the method significantly reduces the inspection time and is more suitable for real time applications. The method can be used to detect smaller flaw sizes and increases the 90/50 probability of detection (POD) to extend to smaller anomaly size ranges than other methods. That is, 90% of anomalies of a certain size can be detected with 50% confidence. Importantly, the method can reliably detect and characterizes flaws at edges that historically have been difficult to identify and analyze.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for inspecting a part comprising:
   providing a part having an edge;
   providing an eddy current apparatus;
   acquiring phase data for at least two phases in at least two different frequencies for the part under inspection using an eddy current probe;
   combining the first phase data into a first single multi-frequency phase image having a plurality of pixels;
   combining the second phase data into a second single multi-frequency phase image having a plurality of pixels;
   preprocessing each of the first and second multi-frequency phase images;
   performing a spatio-temporal correlation on each preprocessed phase image to produce a correlation feature;
   performing a thresholding operation on the correlation feature of each preprocessed phase image to produce a binary first phase image and a binary second phase image, wherein a threshold value used in the step of performing the thresholding operation on each preprocessed phase image is based on that image; and
   combining the produced binary images to generate a single image.

2. The method of claim 1, further comprising pruning a portion of the generated single image.

3. The method of claim 1, further comprising identifying an anomaly signature on the generated single image.

4. The method of claim 3, further comprising estimating anomaly size.

5. The method of claim 4, further comprising generating a report identifying anomaly features.

6. The method of claim 1, wherein acquiring phase data for at least two phases comprises acquiring horizontal and vertical channel data.

7. The method of claim 1, wherein acquiring data for two frequencies in a single phase occurs simultaneously.

8. The method of claim 1, wherein the thresholding operation comprises
   calculating a ratio of pixels thresholded with respect to the total number of pixels in the preprocessed phase image at different signal values;
   calculating a difference between consecutive signal value ratios;
   recording decimal position values for each difference; and
   defining a decimal value threshold.

9. The method of claim 1, wherein the preprocessing comprises:
   applying a low pass filter, a de-blurring filter, a high pass filter, a smoothing filter or a combination thereof 10. The method of claim 1, wherein the phase data is acquired for two different phases and wherein the data acquired for the first phase is acquired using the same frequencies as the data acquired for the second phase.

11. A method for inspecting a part comprising:
    providing a part having a non-planar surface;
    providing an eddy current apparatus;
    acquiring horizontal and vertical channel data in at least two different frequencies for the part under inspection using an eddy current probe;
    combining the horizontal channel data into a single multi-frequency horizontal image having a plurality of pixels;
    combining the vertical channel data into a single multi-frequency vertical image having a plurality of pixels;
    preprocessing each of the horizontal and vertical images;
    performing a spatio-temporal correlation on each preprocessed image to produce a correlation feature;
    performing a thresholding operation on the correlation feature of each preprocessed image to produce a binary horizontal image and a binary vertical image, wherein a threshold value used in the step of performing the thresholding operation on each preprocessed phase image is based on that image;
    combining the binary vertical and horizontal images to generate a single image;
    pruning a region of interest;
    identifying an anomaly signature region;
    determining an anomaly feature; and
    reporting the anomaly feature.

12. The method of claim 11, wherein the thresholding operation comprises
    calculating a ratio of pixels thresholded with respect to the total number of pixels in the preprocessed image at different signal values;
    calculating a difference between consecutive signal value ratios;

recording decimal position values for each difference; and
defining a decimal value threshold.

13. The method of claim 11, wherein the preprocessing comprises:
applying a low pass filter, a de-blurring filter, a high pass filter, a smoothing filter or a combination thereof 14. The method of claim 11, wherein the horizontal and vertical channel data is acquired using a single coil eddy current probe.

15. The method of claim 11, wherein the calculated anomaly feature is selected from the group consisting of maximum signal amplitude, number of pixels, energy, and entropy.

16. The method of claim 11, wherein the calculated anomaly feature is a crack size.

17. The method of claim 11, wherein the non-planar surface is an edge.

* * * * *